United States Patent [19]
Friedrich et al.

[11] Patent Number: 5,982,848
[45] Date of Patent: Nov. 9, 1999

[54] X-RAY DIAGNOSIS MACHINE HAVING DISPLACEABLE MEASUREMENT FIELD

[75] Inventors: Joerg Friedrich, Buckenhof; Ulrike Palm-Plessmann, Fuerth, both of Germany

[73] Assignee: Siemens Aktiengesellschaft, Munich, Germany

[21] Appl. No.: 08/933,005

[22] Filed: Sep. 18, 1997

[30] Foreign Application Priority Data

Sep. 18, 1996 [DE] Germany .................. 196 38 145.2

[51] Int. Cl.⁶ .................................................. G03B 42/02
[52] U.S. Cl. .......................... 378/96; 378/97; 378/108
[58] Field of Search ................... 378/96, 97, 108, 378/146

[56] References Cited

U.S. PATENT DOCUMENTS 4,953,192  8/1990  Plewes ...................................... 378/146
5,210,782  5/1993  Geluk et al. ............................. 378/146
5,307,396  4/1994  Tsuchino ................................. 378/146

FOREIGN PATENT DOCUMENTS 1860908  8/1962  Germany .
3310971  9/1984  Germany .

*Primary Examiner*—David P. Porta
*Attorney, Agent, or Firm*—Sughrue, Mion, Zinn, Macpeak & Seas, PLLC

[57] ABSTRACT

An X-ray diagnosis machine having an X-ray source (3) and a recording device with a photo-timer which has at least one measurement field (2) in a radiation detector plane (1) essentially parallel to the image plane. The measurement field is mounted so as to be capable of being displaced in the radiation detector plane.

4 Claims, 2 Drawing Sheets

X-RAY DIAGNOSIS MACHINE HAVING DISPLACEABLE MEASUREMENT FIELD

The following disclosure is based on German Patent Application No. 19638145.2, filed on Sep. 18, 1997.

FIELD OF AND BACKGROUND OF THE INVENTION

The invention relates to new and useful improvements in X-ray diagnosis machines. More particularly, the invention relates to an X-ray diagnosis machine having an X-ray source and an image recording device with a photo-timer. The photo-timer has at least one measurement field in a radiation detector plane which is essentially parallel to the image plane.

Modern X-ray recording machines are increasingly making use of a photo-timer to control exposure (intensity and duration). An important component of such photo-timers are so-called measurement fields (sensors). These measure the radiation impinging on the X-ray detector located behind the trans-irradiated object and control the beam generation via an electronic system. The purpose thereof is ensuring correct exposure of the X-ray detector, which in conventional systems is often an X-ray film, but which is now often some other type of detector, for example a so-called X-ray image intensifier or other type of electronic detector (e.g. aSi/Se).

The measurement fields or sensors are typically arranged at fixed positions distributed over a surface (in this respect reference is made, for example, to the product descriptions of Siemens: DIGISCAN 2T or Philips: THORAVISON). The objects to be radiographed must therefore be brought into the beam path between the X-ray source and the detector so as to cover at least one sector of the measurement fields. This sector is then used exclusively to control the recording operation. However, such positioning squarely in front of the measurement field is not always possible when the patient is a child, or a person who is badly injured or severely disabled.

To solve this problem, the user has to take so-called "free", i.e. manual, non-automated exposures without the assistance of measurement fields. This can result in faulty exposures and an increased radiation burden for the patient, owing to the possibility that repeated pictures may need to be taken.

German Laid-Open Publication DE 33 10 971 A1 discloses an X-ray diagnosis machine which addresses this problem by arranging a plurality of measurement fields so that they are distributed over a surface corresponding to the total surface of the image recording part. A computer compares the selected radiation field size on the detector of the photo-timer with the selected measurement fields and switches off any measurement fields that are not situated completely within the radiation field. Although this arrangement circumvents the problem described above, it is very expensive in terms of both the outlay for construction and the cost and complexity of the associated electronic evaluation system.

OBJECTS OF THE INVENTION

It is therefore an object of the invention to further improve upon X-ray diagnosis machines of the type described above. Another object of the invention is to provide an X-ray diagnosis machine which allows optimum exposure control and is of simple design. Yet another object is to provide an x-ray diagnosis machine that avoids component redundancy while at the same time providing reliably accurate photo-timer exposure measurements.

SUMMARY OF THE INVENTION

These and other objects are achieved by the teaching of claim 1. Particularly advantageous refinements of the invention are the subject matter of the dependent claims.

Specifically, an X-ray diagnosis machine according to the invention has a measurement field mounted such that it can be displaced in the radiation detector plane, under positive control and in concert with movements imparted to the X-ray source.

Preferably, the measurement field tracks the movements of the X-ray source either by using position sensors on the motive device of the X-ray source or by using radiation sensors arranged on the measurement field. According to one particular embodiment, the measurement field sensors themselves can be used to control the movement of the measurement field. Whether the above-described position sensors or the radiation sensors are used, in either case, the signals output by the sensors are used to supply the required drive signals to the displacement device for the measurement field.

It should be noted that, since guides and electric supply leads of the measurement field are generally situated in the beam path upstream of the X-ray detector, they, just like the measurement field itself, should be sufficiently transparent to the X-ray radiation employed so as to avoid an adverse effect on image quality.

BRIEF DESCRIPTION OF THE DRAWINGS

The invention, including further advantageous features and refinements of the invention, is explained in more detail below with the aid of diagrammatic, exemplary embodiments in the drawing.

In the drawing.

DETAILED DESCRIPTION OF THE PREFERRED EMBODIMENTS

Figure 1:
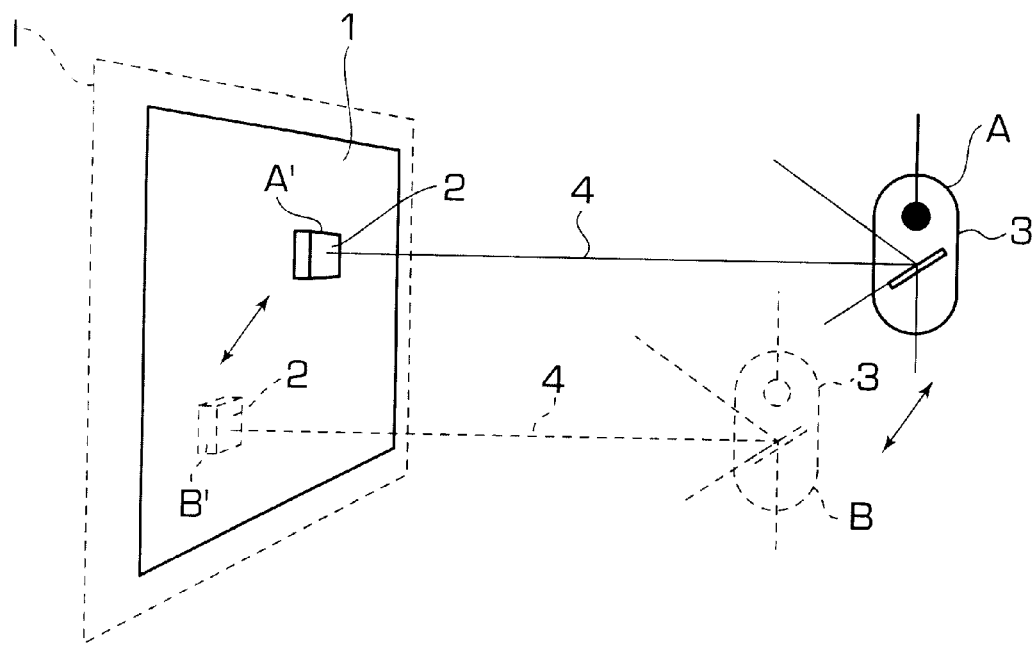
FIG. 1 shows the displacement of the measurement field in the beam detector plane in accordance with the movement of the X-ray source.

According to a first embodiment, an X-ray detector (e.g., film detector or electronic detector), which is represented only schematically in FIG. 1 by way of an image plane I, is generally located parallel to the beam detector plane 1 in the beam path downstream of the measurement field 2. Position A' or B' in the measurement field 2 in the beam detector plane is determined by position sensors in guides of the detector and of the measurement field. Position A or B of the X-ray source 3 in geometrical space is determined in a corresponding manner via position sensors in its guides. A movement of the X-ray source 3, for example from position A to position B, is picked up electronically and used to determine a new position B' for the measurement field 2. The measurement field 2, which has two-dimensional freedom of movement in the radiation detector plane, is then brought into the new position B', for example by a motor.

The pairs of positions A–A' and B–B' are generally selected such that the measurement field 2 is located in the central beam 4 of the X-ray source 3. Moreover, seen from the X-ray source 3, the central beam 4 is usually aimed at the center of the object to be radiographed (not shown). Accordingly, since the measurement field "follows" the X-ray source 3 automatically through the operation of the position sensors, motors, etc., the operator of the X-ray diagnosis machine need be concerned only with correctly centering the beam 4 on the object to be radiographed, e.g., a patient. Once the X-ray source 3 has been correctly positioned with respect to that object, the central beam 4 will correctly pass through the object being radiographed, through the measurement field 2 of the photo-timer, and onto the X-ray detector. The photo-timer operates in a conventionally known manner to control, e.g., the intensity and duration of the radiation emitted from the X-ray source 3, and thereby ensures correct exposure of the X-ray detector.

Should the squarely aimed alignment as described above not be desired, the X-ray diagnosis machine according to the invention permits the use of appropriate displacement offsets. For example, appropriate parameters for offsetting the measurement field 2 from the centered position A' or B' can be entered into the electronic system of the X-ray diagnosis machine manually or through manual selection of predefined offsets programmed into memory.

Figure 2:
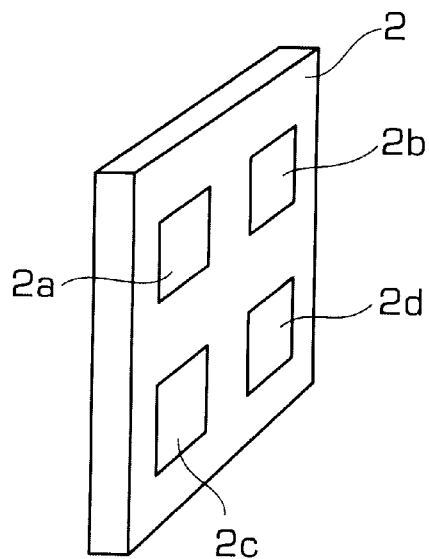
FIG. 2 shows the division of a measurement field into measurement subfields, e.g. for the purpose of accommodating eccentric object trans-radiation.

FIG. 2 illustrates a further embodiment, wherein a measurement field 2 is split into a plurality of measurement subfields 2a to 2d which occupy different geometric positions. Preferably, these subfields are activated and evaluated individually. Such an arrangement is particularly useful whenever the X-ray diagnosis machine is used for eccentric irradiation procedures.

Figure 3:
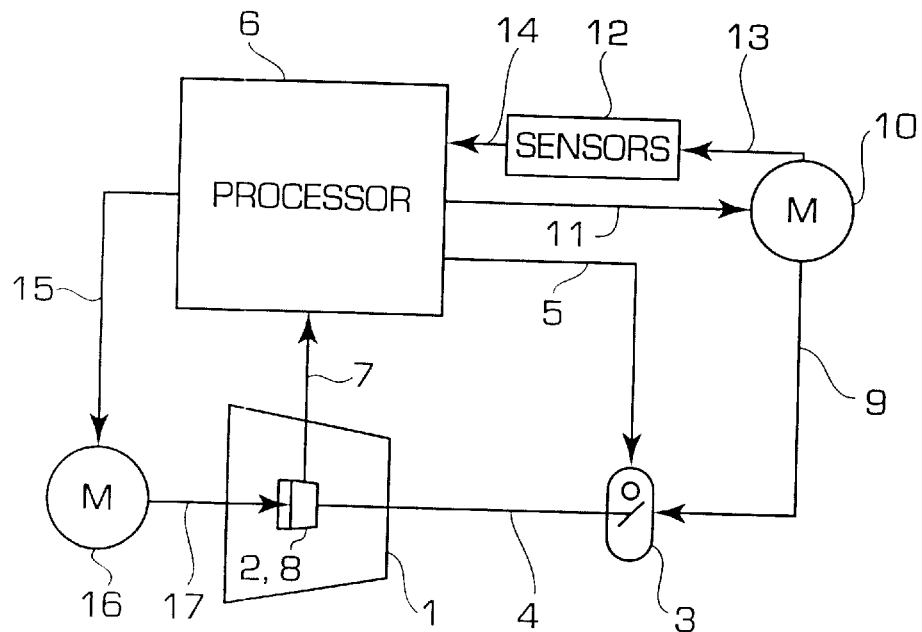
FIG. 3 shows one embodiment of a system for positioning the measurement field correctly with respect to the X-ray source.

FIG. 3 shows one embodiment of a system for positioning the measurement field correctly with respect to the X-ray source. Other portions of the overall X-ray diagnosis machine not directly related to the positioning system are omitted from the figure for the sake of clarity. As shown, the system includes an X-ray source 3 that can be controlled in various respects. For example, its exposure settings are controlled by signals 5 output by a processing unit 6 in accordance, inter alia, with exposure readings 7 input to the processor 6 from the measurement field 2 of a photo-timer 8. The X-ray source 3 is additionally controlled in its physical location relative to a point in the radiation detector plane 1 by means of drive signals 9 output by a drive unit 10. The drive unit 10, in turn, is controlled by motor control signals 11 also originating from the processing unit 6 in response, e.g., to user-input commands.

One or more position sensors 12 are electrically connected to the drive unit 10 is such a way that they receive signals 13 indicative of the current position and movement of the X-ray source 3. Alternatively to the embodiment illustrated, the position sensors 12 can be arranged to receive location information from the X-ray source 3 directly. For example, as described with respect to FIG. 1, the position sensors can be arranged in guides of the X-ray source 3. In either case, the sensors 12 output position information signals 14 to the processing unit 6. The position information signals 14 are processed within the processing unit 6 in such a manner that the processing unit 6 outputs position adjustment signals 15 to a displacement device 16. The displacement device 16, in turn, outputs signals 17, to adjust the position of the photo-timer measurement field 2 within the radiation detector plane 1 as described above with reference to FIG. 1.

In operation, any movements imparted to the X-ray source 3 through the processing unit 6 and drive unit 10 are sensed by the sensors 12. These movements are then tracked by the measurement field 2, through operation of the processing unit 6 and the motor 16, in such a manner that a predetermined positional relationship is maintained between the measurement field 2 and the X-ray source 3. In most cases, this positional relationship will be one whereby the central beam 4 of the X-ray source 3 passes orthogonally first through the object being irradiated (not shown), then through the detector plane 1 and finally through the image plane (not shown). If other irradiation orientations are for some reason desired, these can be accommodated by inputting appropriate offset values into the processing unit 6.

Figure 4:
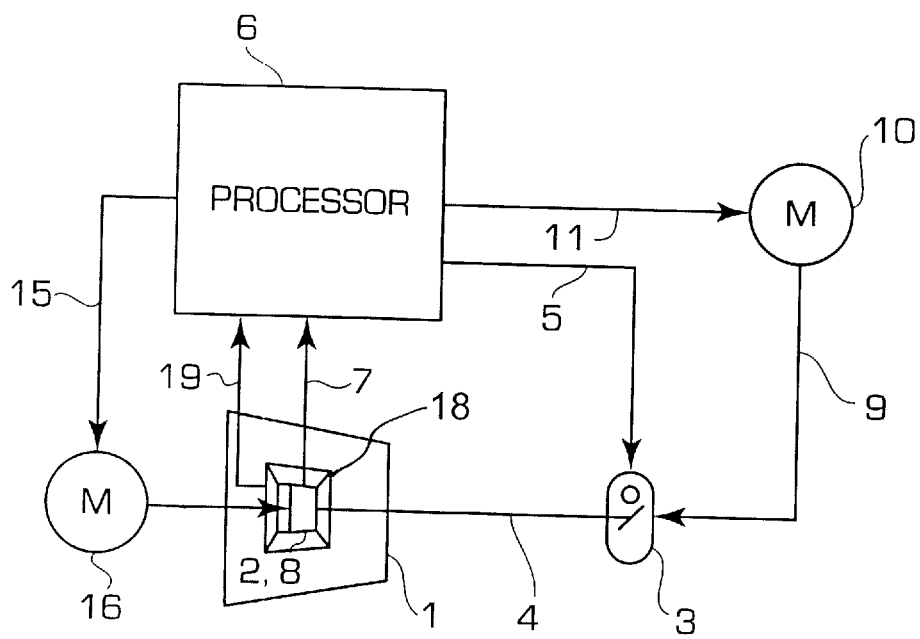
FIG. 4 shows an alternative embodiment to the one shown in FIG. 3, wherein the positioning of the measurement field is controlled using a radiation sensor arranged on the measurement field.

FIG. 4 illustrates an alternative embodiment to the one shown in FIG. 3, wherein the movement of the measurement field 2 is controlled using a radiation sensor 18 arranged on the measurement field 2. In this embodiment, the sensors 12 are omitted and, instead, the radiation sensor 18 determines the current location and movement direction of the X-ray source 3 by tracking the central beam 4 being emitted by the X-ray source. The sensor 18 supplies position information signals 19 to the processing unit 6. The processing unit 6 then converts the position information signals 19 into appropriate position adjustment signals 15, which are output to the displacement device 16 as described with respect to the embodiment of FIG. 3. The tracking control function itself can be realized, e.g., through comparator processing, whereby, e.g., individual sectors of the sensor 18 seek to maximize the intensity of the radiation impinging on each of the individual sectors.

According to one variation on the embodiment of FIG. 4, the sensors 18 are provided not on the measurement field 2 itself but rather in guides in which the measurement field 2 runs, as described with respect to FIG. 1. According to another embodiment, separate sensors 18 are not needed if the actual measurement field sensors 2 are used for generating the signals for the tracking movement of the measurement field as well.

As described in detail above, the present invention provides an X-ray diagnosis machine enhanced by a system that automatically and accurately positions a photo-timer measurement field in appropriate alignment with respect to a movable X-ray source. By rendering the measurement field movable within the radiation detector plane so as to remain in alignment with the X-ray source, the system according to the invention avoids unnecessary redundancy of measurement fields and avoids inaccurate X-ray exposures that can result if the measurement field is not correctly centered in the X-ray beam path behind the object being trans-radiated.

The above description of the preferred embodiments has been given by way of example. From the disclosure given, those skilled in the art will not only understand the present invention and its attendant advantages, but will also find apparent various changes and modifications to the structures disclosed. It is sought, therefore, to cover all such changes and modifications as fall within the spirit and scope of the invention, as defined by the appended claims, and equivalents thereof.

What is claimed is:

1. An X-ray diagnosis machine comprising:
   a movable X-ray source;
   an image recording device including an X-ray detector situated substantially in an image plane;
   a photo-timer including at least one measurement field mounted displaceably in a radiation detector plane that is essentially parallel to the image plane; and
   means for displacing the measurement field in two dimensions in the radiation detector plane, whereby the displacement of the measurement field is performed under positive control of said X-ray source in concert with movements of said X-ray source.

2. The X-ray diagnosis machine as claimed in claim 1, further comprising:

a means for displacing said X-ray source; and at least one position sensor that senses displacements of said X-ray source;

wherein:

said means for displacing the measurement field comprises a motive device; and said motive device is driven in accordance with signals output by said means for displacing said X-ray source.

3. The X-ray diagnosis machine as claimed in claim 1, further comprising:

at least one radiation sensor arranged on the measurement field;

wherein:

said means for displacing the measurement field comprises a motive device; and said motive device is driven in accordance with signals output by said radiation sensor.

4. System for positioning a measurement field of a photo-timer in an X-ray diagnosis machine, comprising:

a signal source for outputting a signal indicative of a current location of an X-ray source;

an actuator for translating the measurement field of the photo-timer within a predetermined area of a radiation detector plane in accordance with the signal output by said signal source such that the measurement field maintains a predetermined positional relationship within the predetermined area relative to the X-ray source.

\* \* \* \* \*